United States Patent
Adams et al.

(10) Patent No.: US 8,957,778 B2
(45) Date of Patent: Feb. 17, 2015

(54) SAMPLING SYSTEM

(75) Inventors: George Adams, Merrimack, NH (US); John Dana Hubbard, Billerica, MA (US); Aaron Burke, Hamilton, MA (US); Anthony DiLeo, Westford, MA (US)

(73) Assignee: EMD Millipore Corporation, Billerica, MA (US)

(*) Notice: Subject to any disclaimer, the term of this patent is extended or adjusted under 35 U.S.C. 154(b) by 565 days.

(21) Appl. No.: 12/452,747

(22) PCT Filed: Jul. 18, 2008

(86) PCT No.: PCT/US2008/008834
§ 371 (c)(1),
(2), (4) Date: May 3, 2010

(87) PCT Pub. No.: WO2009/017612
PCT Pub. Date: Feb. 5, 2009

(65) Prior Publication Data
US 2010/0201521 A1    Aug. 12, 2010

Related U.S. Application Data

(60) Provisional application No. 60/963,016, filed on Aug. 2, 2007.

(51) Int. Cl.
*A61J 1/00* (2006.01)
*G01N 1/18* (2006.01)
(Continued)

(52) U.S. Cl.
CPC . *G01N 1/18* (2013.01); *B01L 3/505* (2013.01); *B01L 3/545* (2013.01);
(Continued)

(58) Field of Classification Search
CPC ............ A61J 2205/60; A61J 1/10; A61J 1/12; A61J 1/14; A61B 2019/44; A61B 2019/448
USPC ................. 340/572.1, 572.7, 572.8; 235/385; 73/863, 863.31, 863.84, 864.91
See application file for complete search history.

(56) References Cited

U.S. PATENT DOCUMENTS 3,726,694 A    4/1973   Rohrer
5,360,437 A    11/1994  Thompson
(Continued)

FOREIGN PATENT DOCUMENTS

CN    1201523 A    12/1998
CN    1658233 A    8/2005
(Continued)

OTHER PUBLICATIONS

"Ramtron Serial FRAM Heavy Ion Test", BNL, Nov. 1998, Document retrieved on May 4, 2011, Available at: http://klabs.org/richcontent/MemoryContent/FRAM/FRAM_SPROM_BNL1198.htm.
(Continued)

*Primary Examiner* — Andrew Bee
(74) *Attorney, Agent, or Firm* — EMD Millipore Corporation

(57) ABSTRACT

The present invention uses a wireless memory/communication device at least on the one or more sample storage devices, preferably on both the one or more sample storage devices and the sampling holder, optionally the port on the equipment as well. Data such as that relating to the vessel, the location of the port on the vessel, the device, its manufacture date or lot number, the date of the installation, sterilization and/or taking of a sample along with the person who installed the device and/or took the sample can be read and preferably added to the wireless device when a read/write type of device as these events occur through a scanner/reader/writer device (fixed or hand held). The sample storage device in the laboratory can also then be read and recorded to track the sample storage device's life.

18 Claims, 5 Drawing Sheets

(51) Int. Cl.
*C12M 1/26* (2006.01)
*B01L 3/00* (2006.01)
*G01N 1/10* (2006.01)
*G01N 1/20* (2006.01)
*G01N 35/00* (2006.01)

(52) U.S. Cl.
CPC .. *B01L 2300/022* (2013.01); *G01N 2001/1031* (2013.01); *G01N 2001/205* (2013.01); *G01N 2035/00782* (2013.01); *C12M 33/00* (2013.01)
USPC ............... 340/572.8; 340/572.1; 340/572.7; 235/385; 73/863; 73/863.31; 73/863.84; 73/864.91

(56) References Cited

U.S. PATENT DOCUMENTS

| | | | |
|---|---|---|---|
| 5,674,381 | A | 10/1997 | Den Dekker |
| 5,866,907 | A | 2/1999 | Drukier et al. |
| 5,892,706 | A | 4/1999 | Shimizu et al. |
| 5,923,001 | A | 7/1999 | Morris et al. |
| 6,032,543 | A | 3/2000 | Arthun et al. |
| 6,140,139 | A | 10/2000 | Lienau et al. |
| 6,285,285 | B1* | 9/2001 | Mongrenier ............... 340/572.8 |
| 6,366,206 | B1 | 4/2002 | Ishikawa et al. |
| 6,617,963 | B1 | 9/2003 | Watters et al. |
| 6,717,154 | B2 | 4/2004 | Black et al. |
| 6,779,575 | B1 | 8/2004 | Arthun |
| 6,795,339 | B2 | 9/2004 | Ooishi |
| 7,048,775 | B2 | 5/2006 | Jornitz et al. |
| 8,028,835 | B2* | 10/2011 | Yasuda et al. ............. 206/459.1 |
| 8,111,159 | B2* | 2/2012 | Andreasson et al. ...... 340/572.1 |
| 8,405,508 | B2 | 3/2013 | Burke |
| 8,497,775 | B2 | 7/2013 | Burke |
| 2001/0007532 | A1 | 7/2001 | Sato et al. |
| 2003/0072676 | A1 | 4/2003 | Fletcher-Haynes et al. |
| 2003/0156449 | A1 | 8/2003 | Ooishi |
| 2003/0164401 | A1 | 9/2003 | Andreasson et al. |
| 2003/0183699 | A1 | 10/2003 | Masui |
| 2004/0173456 | A1 | 9/2004 | Boos et al. |
| 2005/0040433 | A1 | 2/2005 | Nozieres et al. |
| 2005/0132821 | A1 | 6/2005 | Furey et al. |
| 2005/0205658 | A1 | 9/2005 | Baker et al. |
| 2005/0210302 | A1 | 9/2005 | Kato et al. |
| 2006/0016897 | A1 | 1/2006 | Yasuda et al. |
| 2006/0092013 | A1 | 5/2006 | Hager et al. |
| 2006/0201263 | A1 | 9/2006 | Furey et al. |
| 2006/0211995 | A1 | 9/2006 | Myhrberg et al. |
| 2006/0220868 | A1 | 10/2006 | Takasawa et al. |
| 2006/0272432 | A1 | 12/2006 | Belongia |
| 2007/0080783 | A1* | 4/2007 | Ghosh et al. ................. 340/10.1 |
| 2007/0217717 | A1 | 9/2007 | Murray |
| 2008/0042837 | A1 | 2/2008 | Burke |
| 2008/0137399 | A1 | 6/2008 | Chan et al. |
| 2010/0006204 | A1 | 1/2010 | Burke et al. |
| 2012/0061463 | A1 | 3/2012 | Burke |
| 2014/0252084 | A1 | 9/2014 | Burke et al. |

FOREIGN PATENT DOCUMENTS

| | | |
|---|---|---|
| CN | 1695161 A | 11/2005 |
| DE | 29819967 U1 | 1/1999 |
| EP | 1001265 A2 | 5/2000 |
| EP | 1754973 A2 | 2/2007 |
| GB | 1325961 A | 8/1973 |
| GB | 1527341 A | 10/1978 |
| JP | 11-297963 A | 10/1999 |
| JP | 11-214741 A | 12/1999 |
| JP | 2003-243631 A | 8/2003 |
| JP | 2005-17177 A | 1/2005 |
| JP | 2005-503669 A | 2/2005 |
| JP | 2005-503870 A | 2/2005 |
| JP | 2005-181336 A | 7/2005 |
| JP | 2006-30035 A | 2/2006 |
| JP | 2006-39773 A | 2/2006 |
| JP | 2006-90937 A | 4/2006 |
| JP | 2006-276033 A | 10/2006 |
| WO | 96/14043 A1 | 5/1996 |
| WO | 97/16715 A1 | 5/1997 |
| WO | 01/08106 A2 | 2/2001 |
| WO | 01/47466 A1 | 7/2001 |
| WO | 03/026724 A1 | 4/2003 |
| WO | 2004/023389 A2 | 3/2004 |
| WO | 2004/028631 A1 | 4/2004 |
| WO | 2006/032326 A1 | 3/2006 |
| WO | 2006/041965 A2 | 4/2006 |

OTHER PUBLICATIONS

"AN200: Advantages of the FM24C16 Serial 16Kb FRAM Memory", Ramtron International Corporation, Jan. 1999, pp. 1-2.

"GammaTag: Gamma Sterilization RFID Tags", GammaTag Brochure, NewAge Industries AdvantaPure, Jun. 17, 2009, 2 pages.

"Memories: Radiation—Test results", Retrieved on May 4, 2011, Document available at: http://klabs.org/richcontent/MemoryContent/mem_pages/mem_rad_results.htm.

"New RFID Tag Withstands Industrial Sterilization", RFID Journal, Dec. 13, 2006, 2 pages.

"Ramtron Vendor Test Reports", Dec. 2, 1996, 15 pages.

Extended European Search Report received for EP Patent Application No. 07253109.8, mailed on Oct. 9, 2007, 6 pages.

Extended European Search Report received for EP patent Application No. 08164914.7, mailed on Mar. 12, 2010, 6 pages.

International Preliminary Report on Patentability received for PCT Patent Application No. PCT/US2008/006834, issed on Feb. 2, 2010, 7 pages.

International Search Report and Written Opinion received for PCT patent Application No. PCT/US2008/008834, mailed on Feb. 18, 2009, 8 pages.

Chu et al., "The Endurance Performance of 0.5 μm FRAM Products", Technical paper, Ramtron International Corporation, May 2005, pp. 1-3.

Kamp et al., "Adaptable Ferroelectric Memories for Space Applications", Non-Volatile Memory Technology Symposium, Nov. 15-17, 2004, pp. 149-152.

Namkung et al., "Raliability and Endurance of FRAM a case study", Non-volatile Memory Technology Symposium, Nov. 4, 2002, 5 pages.

Nguyen et al., "Radiation Response of Emerging FeRAM Technology", Nonvolatile Memory Workshop, Nov. 7, 2001, pp. 1-3.

Philpy et al., "Reliability of Ferroelectric Memory for High-Rel and Space Applications", Cells Semiconductor Corporation, Presented at the Jet Propulsion Laboratory MRQ conference, Oct. 1999, pp. 1-5.

Takasu, Hidemi, "Ferroelectric memories and their applications", Microelectronic Engineering, vol. 59, No. 1-4, Nov. 2001, pp. 237-246.

"Total Dose Radiation Tests at FRAM Non-Volatile Memories", vH&S Internal Memo, Nov. 30, 1996, pp. 1-5.

Non-Volatile Memory Technology Symposium, Cells Semiconductor Corporation, Nov. 2000, pp. 1-3, "Advances in FeRAM Technologies", Derbenwick, et al.

Non-Volatile Memory Technology Symposium, Celis Semiconductor Corporation, Nov. 2000, Advances in FeRAM Technology Slide presentation, 23 pages, Derbenwick, et al.

News Release of RFID International Business Association, et al., Feb. 28, 2006, "RFID Accredited Workshop Added to INTERPHEX2006 Pre-Conference Program/Recent FDA Symposium Exposes Importance of RFID Education", 3 pages.

EE Times India, posted Aug. 12, 2005, www.eetindia.co.in/ART..., "RF/Wireless Design, RFID Tag with 256 bytes of FRAM", 1 page.

Business Wire, Dec. 10, 2003, www.thefreelibrary.com/_/print/PrintArticle.aspx?id=111091130, "RF Saw, Inc. Announces Gamma Radiation Hard RFID Tags; Doses Up to 5 Mega Rads—500 Million Ergs/Gm—With No Measurable Degradation", 1 page.

J. Appl. Phys. 66 (3), Aug. 1, 1989, pp. 1444-1453, "Radiation effects on ferroelectric thin-film memories: Retention failure mechanisms", Scott, et al.

Electronic News, Jun. 6, 1994, 2 pages, "Motorola signs ferroelectric RAM deal", Krause.

Fujitsu Microelectronics America, Inc. News Release, Aug. 9, 2005, www.fujitsu.com/us/news/pr/fma_20050809.html, 2 pages,

(56) References Cited

OTHER PUBLICATIONS

"Fujitsu Introduces New, Light, Cost-Effective RFID Tags with 256 Bytes of FRAM for Product Tracking, Distribution Applications".
Patient Safety, Apr. 26, 2006, 1 page, http://medicalconnectivity.com/2006/04/26/could-saw-rfid-tags-serv..., "Could SAW RFID Tags Serve Health Care?", GEE.
IEEE Circuits & Devices, Jan. 2001, pp. 20-30, "Ferroelectric Memory: On the Brink of Breaking Through", Derbenwick, et al.
IEEE Transactions on Nuclear Science, vol. 41, No. 3, Jun. 1994, pp. 495-502, "A Study of Radiation Vulnerability of Ferroelectric Material and Devices", Coic, et al.
Fujitsu Limited News Release, Feb. 27, 2003, "Fujitsu Develops High Capacity, High Speed Chip with Embedded FRAM for RFID Tags", 3 pages.
IEEE Transactions on Nuclear Science, vol. 38, No. 6, Dec. 1991, pp. 1410-1414, "Radiation Evaluation of Commercial Ferroelectric Nonvolatile Memories", Benedetto, et al.
Escort Memory Systems Lead Sheet, Interphex Trade Show, New-Age-Advantapure discussions, Mar. 21, 2006 and May 10, 2006, 1 page.
NewAge Industries Purchase Order, Jul. 25, 2006, order of 2500 gamma radiation resistant RFID tags from EMS, 1 page.

\* cited by examiner

SAMPLING SYSTEM

CROSS REFERENCE TO RELATED APPLICATIONS

This application is the U.S. National Stage Application of International Application No.: PCT/US2008/008834, filed on Jul. 18, 2008, which claims priority to U.S. Application No. 60/963,016, filed Aug. 2, 2007.

The present invention relates to a sampling system. More particularly, it relates to a sampling system having a port and one or more sample containers that are wirelessly enabled to track location and/or other information.

BACKGROUND

Traditional sample systems for pharmaceutical or biopharmaceutical processes use large stainless steel systems that include steam traps and the like to at least aseptically clean the system between uses.

U.S. Pat. No. 6,032,543 introduced a disposable sterile sampling system comprised of a carousel or holder into which one or more septum containing sampling collection devices are attached. This is sold as the NovaSeptum® sampling device available from Millipore Corporation of Billerica, Mass. The devices have a sample taking device, in this instance a septum surrounding a needle at the front end with the rear portion of the needle being attached to a flexible conduit such as a tube or hose which in turn is attached to a sample storage device such as a bag as shown in the patent or as a syringe as described in US 2006/0211995 A1 and sold as the NovaSeptum® AV system by Millipore Corporation of Billerica. Mass. The internal area between the septum and sample storage device, in the first instance a bag and in the syringe its inner volume, is isolated from the environment and sterilized (gamma or beta radiation, ETO, etc) before assembly into a holder. The holder is liquid tightly attached to a port of a bioreactor or other piece of equipment such as a storage vessel, mixing vessel and the like, the septum based sample taking devices are loaded into the holder and then the face of the system (holder and septum of the sample taking device) is sterilized along with the rest of the interior of the equipment. The vessel is then filled and samples are taken as needed during processing. Information concerning the sample, when and where it was taken and by whom is recorded by hand either onto a paper label that is then attached to the sample storage device or in a notebook.

US 2005/0132821A1 and US2006/0201263A1 add to this concept by eliminating the need for a septum and yet provide a sterile connection and sample collection system. The use of shafts mounted in a holder with tubes connected to the rear portions of the shafts which in turn are connected to s sample storage device such as bags. The shafts are mounted in the holder or body and isolated from the environment and then sterilized by radiation such as gamma or beta, steam, ETO or the like.

US 2006/0272432A1 is also a septum-less system that uses slidable gates to selectively open or close a pathway from the vessel to a conduit and then to a sample storage device.

All of these systems are then mounted to a port and the face of the port is sterilized with the interior of the vessel to provide a sterile pathway for the samples. The shafts are moved either linearly or rotationally into alignment to draw a sample or the gates are moved linearly to open a passage for the liquid sample. As with the NovaSeptum design discussed above, the information is recorded separately and then attached to the sample holder or placed in a notebook.

What is needed is a better method and device for tracking such information in a foolproof manner.

SUMMARY

The present invention uses a wireless memory/communication device at least on the one or more sample storage device such as bags, bottles or syringes, preferably on both the one or more sample storage device and the sampling holder, optionally the port on the equipment as well.

The use of RFID, Zigbee®, Bluetooth® and other wireless systems is acceptable.

In one embodiment, a read only tag, such as a read only RFID tag is used on the one or more sample storage devices. The tag(s) contain an identity code for the sample storage device. This is then used with a scanner (hand held or fixed) to track the usage of this sample storage device such as the date of installation and on which sampling holder, the date of sample taking and the like.

Preferably, the sample storage device utilizes a read/write memory device, such as a RFID, Zigbee®, Bluetooth® and other wireless read/write tag. Data such as that relating to the vessel, the location of the port on the vessel, the date of the installation, sterilization and/or taking of a sample along with the person who installed the device and/or took the sample can be added to the tag on the sample storage device as these events occur through a scanner/reader/writer device (fixed or hand held). The sample storage device in the laboratory can also then be read and recorded to track the sample storage device's life.

More preferably, the system itself, such as the holder also has a memory/communication device and it can transfer its information to the device on the sample storage device, either directly or through an intermediate reader/writer.

IN THE FIGURES

DETAILED DESCRIPTION

Figure 1:
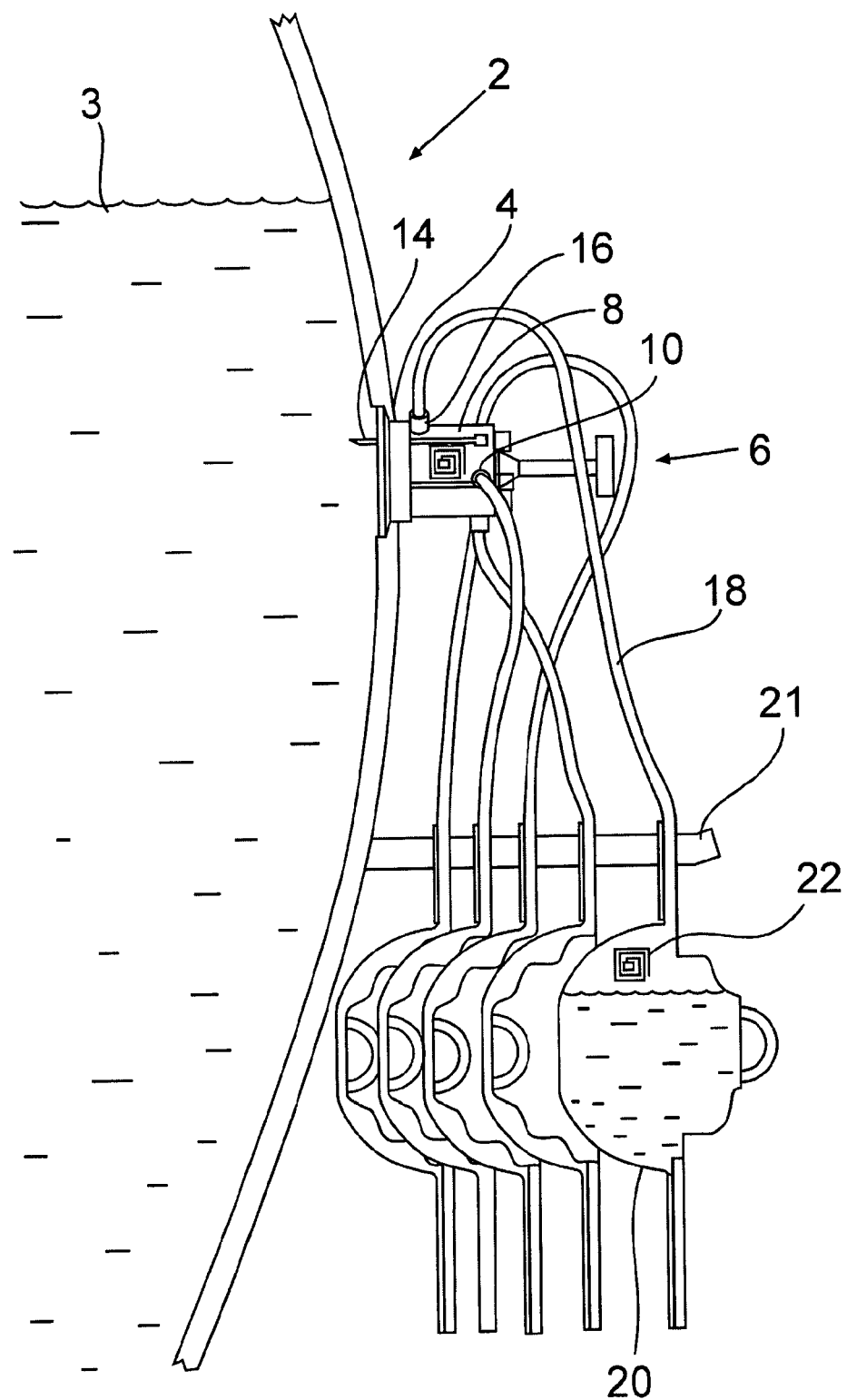
FIG. 1 shows a first embodiment of the present invention in cross-sectional view.

FIG. 1 shows a first embodiment of the present invention. A vessel 2, such as a bioreactor, storage vessel, mixing tank and the like, contains one or more ports 4 (one shown) such as an Ingold® port or a NovaSeptic® port onto or into which a sampling system 6 is mounted. The vessel 2 contains a liquid 3 that needs to be sampled from time to time. In this example, a NovaSeptum® sampling system, according to U.S. Pat. No. 6,032,543 is shown. The system 6 has a holder 8 mounted to the port 4 of the vessel 2. One or more sample sterile collectors 10 are loaded in the holder 8.

The collectors 10 have a septum (not shown) containing a sample gatherer 14 that is open to the remainder of the collector 10 when inserted into the vessel 2. In this instance it is a needle that passes through a septum (not shown) to enter the vessel 2 and collect a sample from the liquid 3. The rear portion 16 of the gatherer 14 is connected to a collection tube 18 which in turn is connected to one or more sample storage devices 20, in this embodiment shown as bags although it may be bottles, syringes or other vessels used to collect and store samples.

The sample storage device(s) 20 each contain a wireless memory/communications device 22 such as a RFID tag, a Zigbee® device, a Bluetooth® device and the like. The wireless device may be mounted to the sample storage device as a plastic encasing disk which covers the wireless device and prevents it from being damaged. Alternatively, it may be laminated onto the sample storage device directly or to a label which is applied to the sample storage device. Such printed labels/wireless devices are known and available from a number of sources including PrintTech and Zebra Technologies. Alternatively, the device may be formed into a plastic tag which has a strap that can be attached to the sample storage device or the tube connected to the sample storage device. In another embodiment, it can be laminated into the film of the sample storage device itself.

Figure 4:
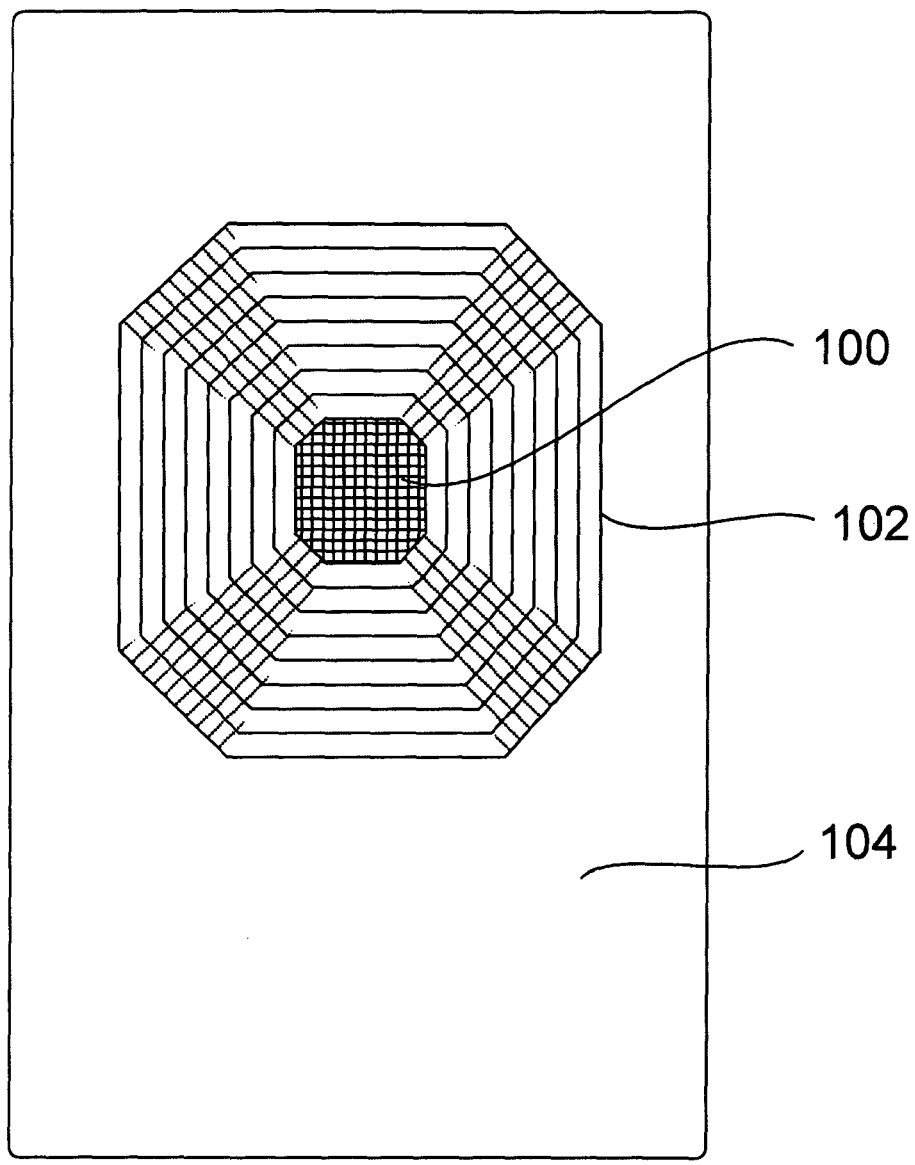
FIG. 4 shows a wireless device useful in the invention in top down planar view.

The wireless device essentially comprises two components as shown in FIG. 4, a microchip 100 and an antenna 102. This is generally attached to a plastic surface or sheet 104 or encapsulated with an epoxy (not shown). The device can be of any frequency although high frequency (HF) and ultrahigh frequency (UHF) are the most popular. Additional elements may be added if desired such as a battery or capacitor to provide the device with its own power source, if desired. Most systems however are passive and rely on the signal from the reader/writer to power up the device as needed.

In this embodiment, the device 22 is a read only device containing at least a unique identifier for that sample storage device, such as an alpha/numeric serial number.

In use, before, during or after the sample storage device(s) 20 have been loaded into the holder 8, they are read by a scanner (not shown) which may be a fixed station such as a desktop reader like the AccuSmart™ reader available from Millipore Corporation of Billerica, Mass. or a hand held device such as the Hose Tracker™ reader available from Advantapure of South Hamilton, Pa.

This information as to the identity of the sample storage device and optionally, at least one trackable-event such as its location, date of installation, installer, etc, can be entered into the scanner. It may be stored there or it may be downloaded to a computer or network connection or the internet if desired.

Upon or just after sampling, the device 22 can again be scanned by the reader to record the use date, time, location, etc.

When the sample storage device 20 reaches the testing laboratory, the device 22 can be scanned to record its arrival and/or analysis. Optionally, the name of the tester, the test to be performed, the storage, length of time before testing and the like may also be added to the scanner or other storage item a computer or network connection or the internet by the laboratory to track its workload and generate its reports.

In the Figures that follow, the same reference numbers are used to if they represent the same elements discussed above in regard to FIG. 1.

Figure 2:
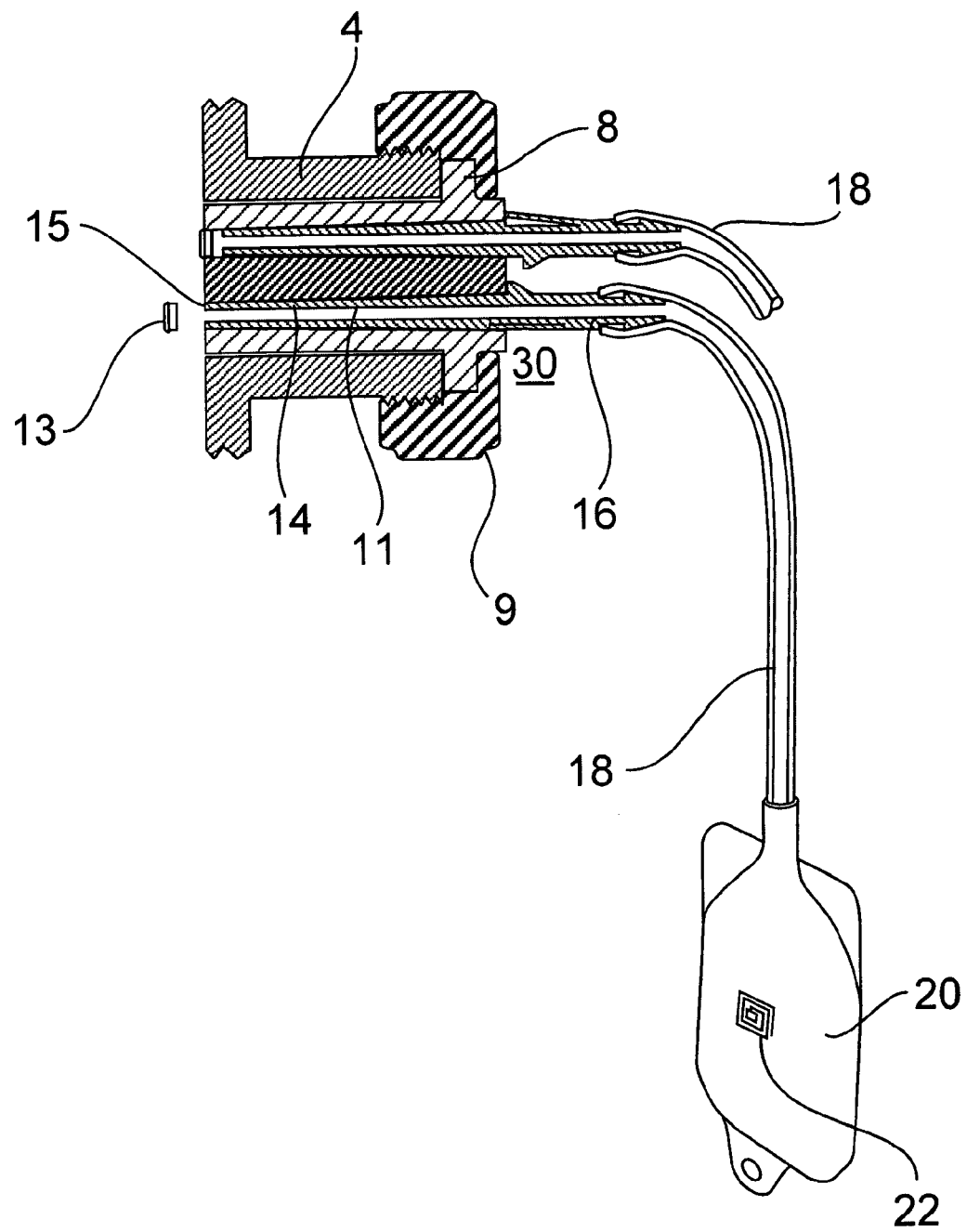
FIG. 2 shows a second embodiment of the present invention in cross-sectional view.

In another embodiment as shown in FIG. 2, the wireless device 22, this time used on a sampling system according to USSN 2005/0132821A1, although a NovaSeptum® system or any other sampling device can also be used, is a read/write device so that data relating to one or more trackable events such as identity, location, installation, use and testing dates and times, etc. can be recorded on to the device 22 itself. Optionally, the data may also be downloaded to a computer, network or internet site as described above in the earlier embodiment. In this embodiment, the holder 8 may be retained to the port by a means such as a nut 9 as shown or by other means such as a clamp. The gatherer 14 in this case is not a needle but rather a shaft having a central bore 11 and the end adjacent the inner volume of the vessel 2 covered by a cap 13. A passageway 15 is behind the cap 13 provides a fluid pathway between the inner volume of the vessel 2 and the central bore of the gatherer 14 when the shaft is extended into the volume to take a sample from the liquid 3. The sample then flows into the tube 18 and sample storage device 20.

An alternative sample device according to USSN 2005/0132821A1 (not shown), which rotates a shaft and the holder relative each other and/or the port to selectively expose and provide access of a shaft to the inner volume of the vessel 2 may be used as well if desired and it functions in a similar manner.

In use, the wireless device 22 arrives at a user's facility with manufacturer and sterilization data, etc. already loaded on to it or contained on a secure website of the manufacturer which can be accessed by providing the website with the identification number contained on the wireless device. When mounted to a vessel 2, various data such as location, date of installation, installer etc. is recorded on the device 22. If desired, the date/time of sterilization of the system 6 in place on the vessel 2 can also be recorded.

When a sample is taken, the day/time/user and other relevant trackable data can be recorded onto the device 22 which is then sterilely disconnected from the system such as by the crimp/crimper cutter device of U.S. Pat. No. 6,779,575 and taken to a laboratory for testing or stored as a retain.

If desired, the date/time of receipt at the lab or the storage facility can be recorded when it is received. Additionally, the data of the device 22 and/or computer, network or internet can also be downloaded and/or updated. Likewise, information regarding the tests conducted, the tester's identification and the like can also be added to the tag.

For storage applications, the device 22 or the computer network or internet site may contain specific storage instructions such as temperature to be maintained at, length for storage and the like.

Figure 3:
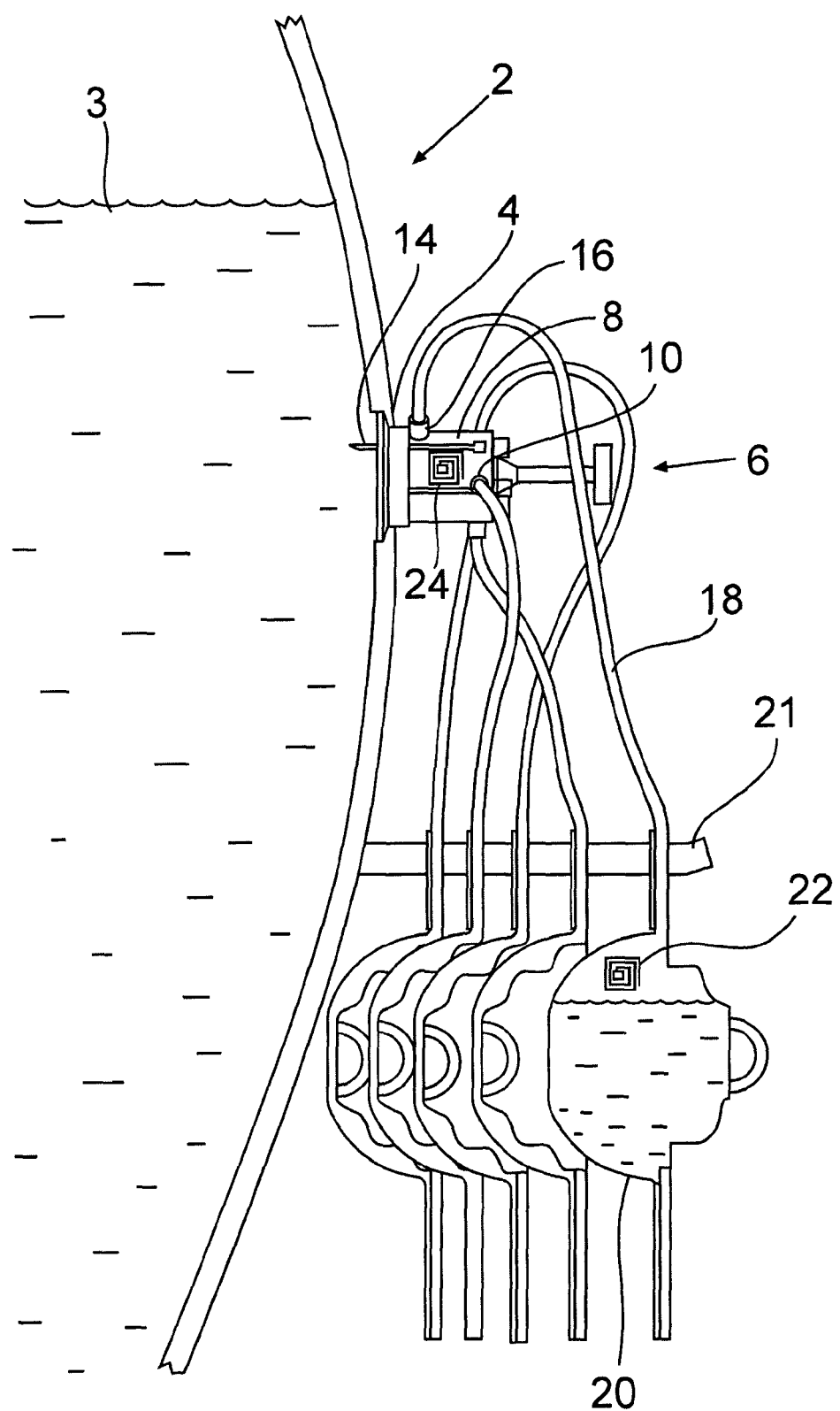
FIG. 3 shows a third embodiment of the present invention in cross-sectional view.

In a third embodiment as shown in FIG. 3, the system 6, such as the holder 8 which holds the sample collectors 10 contains its own wireless memory/communication device 24.

In this way, information relating to the system 6 such as manufacturing information, installation data, sterilization data, loading data (of collectors 10), location on the vessel 2 and/or in the facility can be loaded onto the second wireless device 24.

One can then scan the second device 24 when adding or using a sampling collector 10 so as to provide the first wireless device 22 of the collector 10 with some or all of the data of the system 6. This may be done directly from the second device 24 to the first device 22 or through an intermediary scanner such as a hand held scanning device (not shown).

Figure 5:
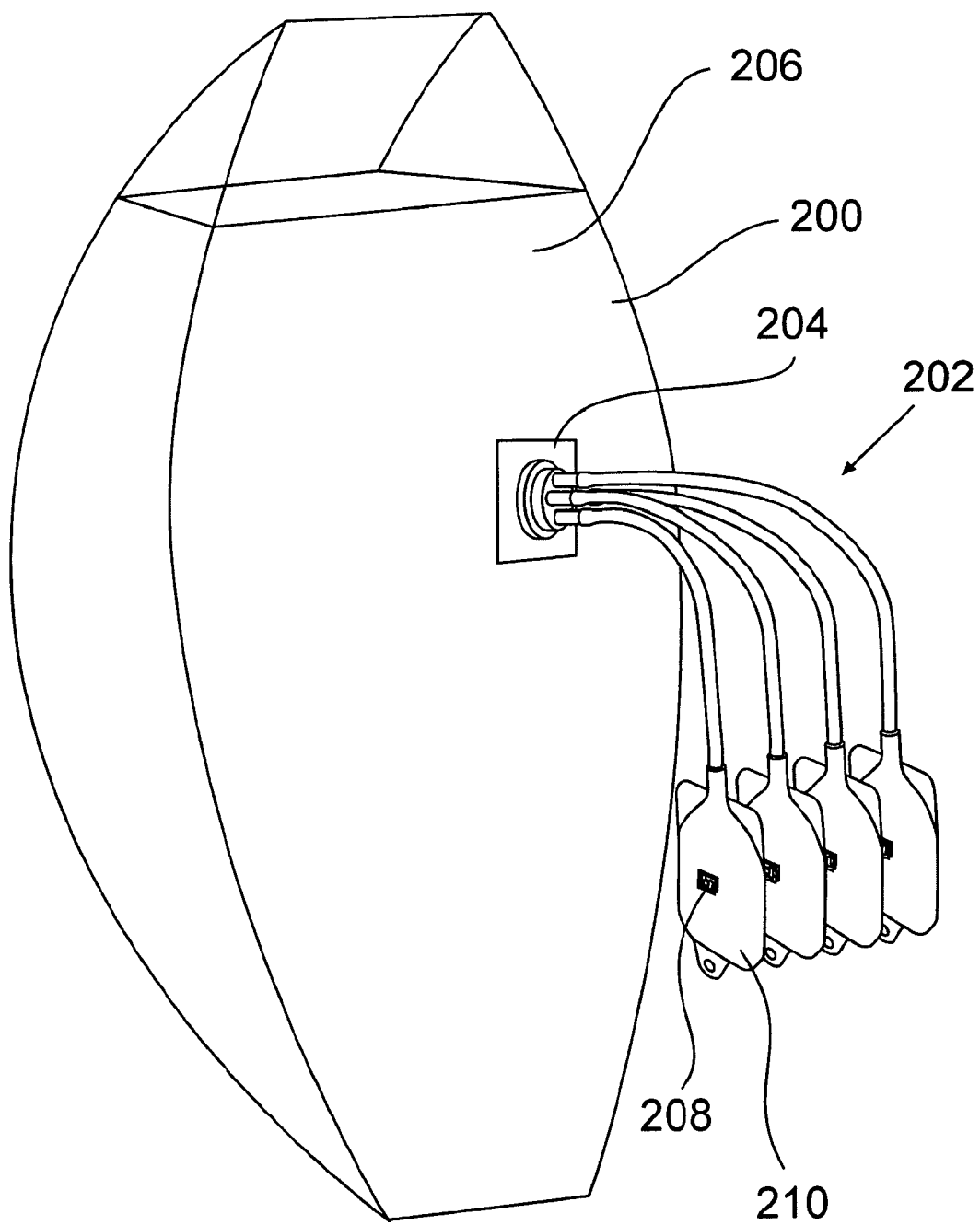
FIG. 5 shows another embodiment of the present invention in planar view.

FIG. 5 shows a sampling device according to the present invention used on a disposable vessel such as a plastic bag or rigid plastic container 200. A sampling system 202 is similar to those discussed above in relation FIG. 1-3 and is attached to the disposable vessel 200 such as by a port 204 which has been attached to an opening (not shown) in the vessel 200. This can be by heat sealing or welding (solvent or sonic energy) the port to or around the opening. Alternatively one can use a threaded fitting that extends through the opening from the interior of the vessel and a nut on the outside that match with the threads to form a liquid tight fitting. Likewise one can use a plastic fitting inside the vessel 200 with a open neck that extends through the opening to the exterior of the vessel 200 and a second piece of plastic that can be sealed to the exterior surface of the neck to hold the fitting in place in the opening in a liquid tight manner. A wireless device 208, at least a read device, and preferably a read/write device as described above is used on at least each of the sample storage device 210. Optionally a second device (not shown) may be attached to the vessel or the port 204 if desired. The vessel 200 and sampling system 202 are made and sealed from the outside environment and then sterilized such as by radiation (gamma or beta), ethylene oxide or the like. If gamma radiation is used, a gamma stable wireless device such as is taught by U.S. Ser. No. 11/501,446, filed Aug. 9, 2006, the teachings of which are incorporated herein by reference.

A sample of the liquid 206 is taken in a manner identical to that described in FIG. 1-3 above.

A process for using the invention comprises providing a collection system such as a NovaSeptum® device having a holder and one or more collection devices mounted therein. Each collection device is formed of a gatherer 14 of some type, such as a septum covered needle, or rigid tube or hollow shaft and the like, a conduit 18 such as a plastic tube attached to a rearward portion of the gatherer 14 and a sample storage device 20 such as a bag, syringe or bottle attached to the rearward portion of the conduit. The collection devices are rendered sterile in their interior before mounting onto the vessel. At least the one or more collection devices 20 contain a wireless communications and information storage device 22 as described herein above. Optionally, the holder 8 also contains a second wireless communications and information storage device 24 as described herein above. The system is mounted to a vessel 2 through a port 4 or opening in a liquid tight manner. The portion of the system that has been exposed to the environment, generally just the face of the holder 8 and the collectors 10 mounted in it is then sterilized in place. Information and if desired, at least one trackable event, on the first wireless device 22, and if present, the second wireless device 24, is taken. This information can be, but is not limited to, identity, location, date of installation, sampling, installer, installation date, etc. The vessel 2 is filled and a sample is taken and information and if desired at least one other trackable event is taken on the first wireless device 22, and if present the second wireless device 24. This information and/or trackable event(s) can be stored on the first and/or second wireless device 22/24 and optionally the scanner (not shown) which may be a fixed station such as a desktop reader like the AccuSmart™ reader available from Millipore Corporation of Billerica, Mass. or a hand held device such as the Hose Tracker™ available from Advantapure of South Hamilton, Pa. Alternatively or additionally, the information may be uploaded to a computer, a control system, a network or an internet address.

A system according to any of the embodiments allows one to electronically collect and/or store one or more trackable events such as data relating to the sampling system, its installation, use and if done, testing results.

By using the sterile disposable sampling systems, one is able to form a liquid tight, hermetic seal between the system and the interior of the vessel so that sterile samples can be taken.

The wireless device enabled system of the present invention eliminates any error as to location, date, time, user and the like and allows one to use good manufacturing practices (GMP) and good laboratory practices (GLP) in sampling systems.

What is claimed:

1. A sample collection system comprising:
    a vessel having an interior containing a sample to be collected within the interior, a port in the vessel providing access to the interior,
    at least one sample storage device, having an interior region for containing a collected sample, an exterior surface, and a port for providing access to the interior region,
    a sample collecting device being formed of a sample collection holder and one or more sample collectors,
    wherein the sample collection holder is liquid tightly sealed to the port in the vessel and attached to the one or more sample collectors,
    wherein each of the one or more sample collectors has a selectively closed front portion, an open rear portion, a passageway providing a fluid pathway between the selectively closed front portion and the open rear portion, and a conduit having upstream and downstream portions,
    wherein the upstream portion of the conduit is connected to the open rear portion of the sample collector,
    and the downstream portion of the conduit is connected to the port of the at least one sample storage device,
    a first wireless memory/communication device directly attached to the exterior surface of a respective one of the at least one sample storage device for the storage of data, and a second wireless memory/communication device directly attached to the sample collection holder,
    wherein information from the second wireless memory/communication device is written to the first wireless memory/communication device when the at least one sample storage device is attached to the sample collection holder.

2. The system of claim 1 wherein the second wireless memory/communication device is a read only device and has data selected from the group consisting of manufacturer, lot number, manufacturing date, sterilization data and combinations thereof.

3. The system of claim 1 wherein the second wireless memory/communication device is a read/write device capable of having data written therein.

4. The system of claim 1 wherein information from the second wireless memory/communication device is directly transferred to the first wireless memory/communication device.

5. The device of claim 1 wherein information from the second wireless memory/communication device is transferred to the first wireless memory/communication device through an intermediary scanner.

6. The system of claim 1 wherein the at least one sample storage device is selected from the group consisting of bags, syringes and bottles.

7. The system of claim 1 wherein the first wireless memory/communication device is laminated directly to the exterior surface of the at least one sample storage device.

8. The system of claim 1 wherein the first wireless memory/communication device is encapsulated by an epoxy and directly mounted to the exterior surface of the at least one sample storage device.

9. The system of claim 1 further comprising a wireless memory/communication device mounted on the port in the vessel.

10. A process of tracking samples comprising the steps of:
    providing a vessel having an interior for containing a liquid to be sampled, and a port in the vessel providing access to the interior,
    providing at least one sample storage device, having an interior region for containing a collected sample, an exterior surface, and a port for providing access to the interior region, and attaching a sample collecting device to the vessel in a liquid tight hermetically sealed manner, the sample collecting device having,
a sample collection holder liquid tightly sealed to the port in the vessel wherein the sample collection holder is attached to a sample collector,
wherein the sample collector has a selectively closed front portion, an open rear portion, a passageway providing a fluid pathway between the selectively closed front portion and the open rear portion, and
a conduit having an upstream portion and downstream portion wherein the upstream portion of the conduit is connected to the open rear portion of the sample collector, and the downstream portion of the conduit is connected to the port on the at least one sample storage device,
a first wireless memory/communication device directly attached to the exterior surface of the at least one sample storage device, and
a second wireless memory/communication device directly mounted to the surface of the sample collection holder,
sterilizing the interior of the vessel and the sample collecting device, filling the vessel with a liquid to be sampled,
copying information from the second wireless memory/communication device to the first wireless memory/communication device when the at least one sample storage device is attached to the sample collection holder, and
scanning the first wireless memory/communication device to determine one or more attributes of the collector and reading the one or more attributes.

11. The process of claim 10 wherein the first wireless memory/communication device is a read/write device and one or more trackable events are loaded onto the first wireless memory/communication device during scanning.

12. The process of claim 10 wherein the at least one sample storage device is selected from the group consisting of bags, syringes and bottles.

13. The process of claim 10 wherein the first wireless memory/communication device is laminated directly to the exterior surface of the at least one sample storage device for the storage of data.

14. The process of claim 10 further comprising a wireless memory/communication device mounted on the port in the vessel.

15. A process of tracking samples comprising the steps of:
providing a system, the system comprising a vessel having an interior for containing a liquid to be sampled,
and a port in the vessel providing access to the interior, and a sample collecting device attached to the vessel in a liquid tight hermetically sealed manner, the sample collecting device having a sample collection holder liquid tightly sealed to the port in the vessel wherein the sample collection holder is attached to a sample collector, wherein the sample collector has a selectively closed front portion, an open rear portion, a passageway providing a fluid pathway between the selectively closed front portion and the open rear portion, wherein the sample collection holder has a second wireless memory/communication device directly mounted to the surface thereof,
attaching a conduit and a sample storage device to the open rear portion, wherein the conduit has an upstream portion and downstream portion wherein the upstream portion of the conduit is connected to the open rear portion of the sample collector, and the downstream portion of the conduit is connected to the port on the sample storage device, wherein the sample storage device has an interior region for containing a collected sample, an exterior surface, and a port for providing access to the interior region to the downstream portion of the conduit and a first wireless memory/communication device directly attached to the exterior surface of the sample storage device,
copying information from the second wireless memory/communication device to the first wireless memory/communication device when the sample storage device is attached or to provide information associated with the system.

16. The process of claim 15, wherein the information is selected from the group consisting of manufacturing information, installation data, location on the vessel and/or in a facility and sterilization data.

17. The process of claim 15, wherein the information is transferred directly from the second wireless memory/communication device to the first wireless memory/communication device.

18. The process of claim 15, wherein the information is transferred from the second wireless memory/communication device to the first wireless memory/communication device through an intermediary scanner.

* * * * *